(12) United States Patent
Waterbury et al.

(10) Patent No.: US 7,122,155 B2
(45) Date of Patent: Oct. 17, 2006

(54) ELECTRON MICROSCOPY CELL FRACTION SAMPLE PREPARATION ROBOT

(75) Inventors: Raymond Waterbury, Montreal (CA); Robert Kearney, Montreal (CA); John Bergeron, Pointe-Claire (CA)

(73) Assignee: McGill University, Montreal (CA)

( * ) Notice: Subject to any disclaimer, the term of this patent is extended or adjusted under 35 U.S.C. 154(b) by 555 days.

(21) Appl. No.: 10/195,309

(22) Filed: Jul. 16, 2002

(65) Prior Publication Data

US 2006/0171850 A1    Aug. 3, 2006

(51) Int. Cl.
*B01L 11/00* (2006.01)
*B01L 3/02* (2006.01)
*G01N 21/00* (2006.01)

(52) U.S. Cl. .............. 422/101; 422/100; 422/103; 422/63; 422/68.1

(58) Field of Classification Search ......... 422/50–105
See application file for complete search history.

(56) References Cited

U.S. PATENT DOCUMENTS

| | | | |
|---|---|---|---|
| 4,427,415 A * | 1/1984 | Cleveland .................. 436/57 |
| 4,797,259 A * | 1/1989 | Matkovich et al. ......... 422/101 |
| 5,792,425 A * | 8/1998 | Clark et al. ................ 422/101 |
| 5,824,224 A * | 10/1998 | Fujishiro et al. ........... 210/651 |
| 5,846,493 A * | 12/1998 | Bankier et al. ............. 422/101 |
| 6,133,045 A * | 10/2000 | Johnson et al. ............ 436/177 |
| 6,159,368 A * | 12/2000 | Moring et al. ......... 210/321.75 |
| 6,315,902 B1 * | 11/2001 | Collasius et al. .......... 210/232 |
| 6,326,212 B1 * | 12/2001 | Aoki .......................... 436/180 |
| 6,402,950 B1 * | 6/2002 | Nix et al. ................ 210/323.2 |
| 6,419,827 B1 * | 7/2002 | Sandell et al. ........ 210/321.75 |
| 6,455,007 B1 * | 9/2002 | Mansky et al. ............ 422/101 |
| 6,464,942 B1 * | 10/2002 | Coffman et al. ........... 422/100 |
| 6,491,873 B1 * | 12/2002 | Roberts et al. ............ 422/101 |
| 6,558,623 B1 * | 5/2003 | Ganz et al. ................. 422/63 |
| 6,592,826 B1 * | 7/2003 | Bloecker et al. .......... 422/101 |
| 6,666,978 B1 * | 12/2003 | Steinel ....................... 210/808 |
| 6,852,290 B1 * | 2/2005 | Hager et al. ............... 422/101 |
| 6,855,553 B1 * | 2/2005 | Bedingham et al. ......... 436/45 |
| 6,896,849 B1 * | 5/2005 | Reed et al. .................. 422/99 |
| 6,899,848 B1 * | 5/2005 | Chen et al. .................. 422/63 |
| 2003/0202909 A1 * | 10/2003 | Atkinson et al. .......... 422/104 |
| 2003/0219360 A1 * | 11/2003 | Olivier ...................... 422/101 |

(Continued)

FOREIGN PATENT DOCUMENTS

EP          1 110 611        6/2001

(Continued)

OTHER PUBLICATIONS

Peter Mitchell, "A perspective on protein microarrays", Nature Biotechnology, Mar. 2002, pp. 225 to 229, vol. 20.

(Continued)

*Primary Examiner*—Brian R. Gordon
(74) *Attorney, Agent, or Firm*—Ogilvy Renault LLP

(57) ABSTRACT

A parallel processing, fluid handling apparatus for concurrent temperature controlled preparation of a plurality of cell fraction samples adapted to be used for electron microscopic viewing. The apparatus comprises generally a sample receiving member, a fluid handling means, and a separation means. The sample receiving member comprises a plurality of discrete apertures each adapted to receive a biological sample therein. The fluid handling means for inserting and removing fluid to and from the plurality of apertures substantially in parallel, permits the biological samples to be processed substantially in parallel by the insertion and removal of processing fluid. The separation means permits the parallel isolated separation of the post-processing samples. The post-processing samples are adapted to be polymerized in embedding solution and removed from the sample receiving member.

24 Claims, 10 Drawing Sheets

U.S. PATENT DOCUMENTS

2003/0226796 A1* 12/2003 Bayer et al. ................. 210/259
2004/0234421 A1* 11/2004 Moll et al. .................. 422/101

FOREIGN PATENT DOCUMENTS

WO     WO 00/72968 A1    12/2000
WO     WO 01/078898     10/2001

OTHER PUBLICATIONS

Pierre Baudhuin, Philippe Evrard, and Jacques Berthet, Electron Microscopic Examination, of Subcellular Fractions I. The Preparation of Representative Samples from Suspensions of Particles, The Journal of Cell Biology, vol. 32, 1967, p. 181-191.

* cited by examiner

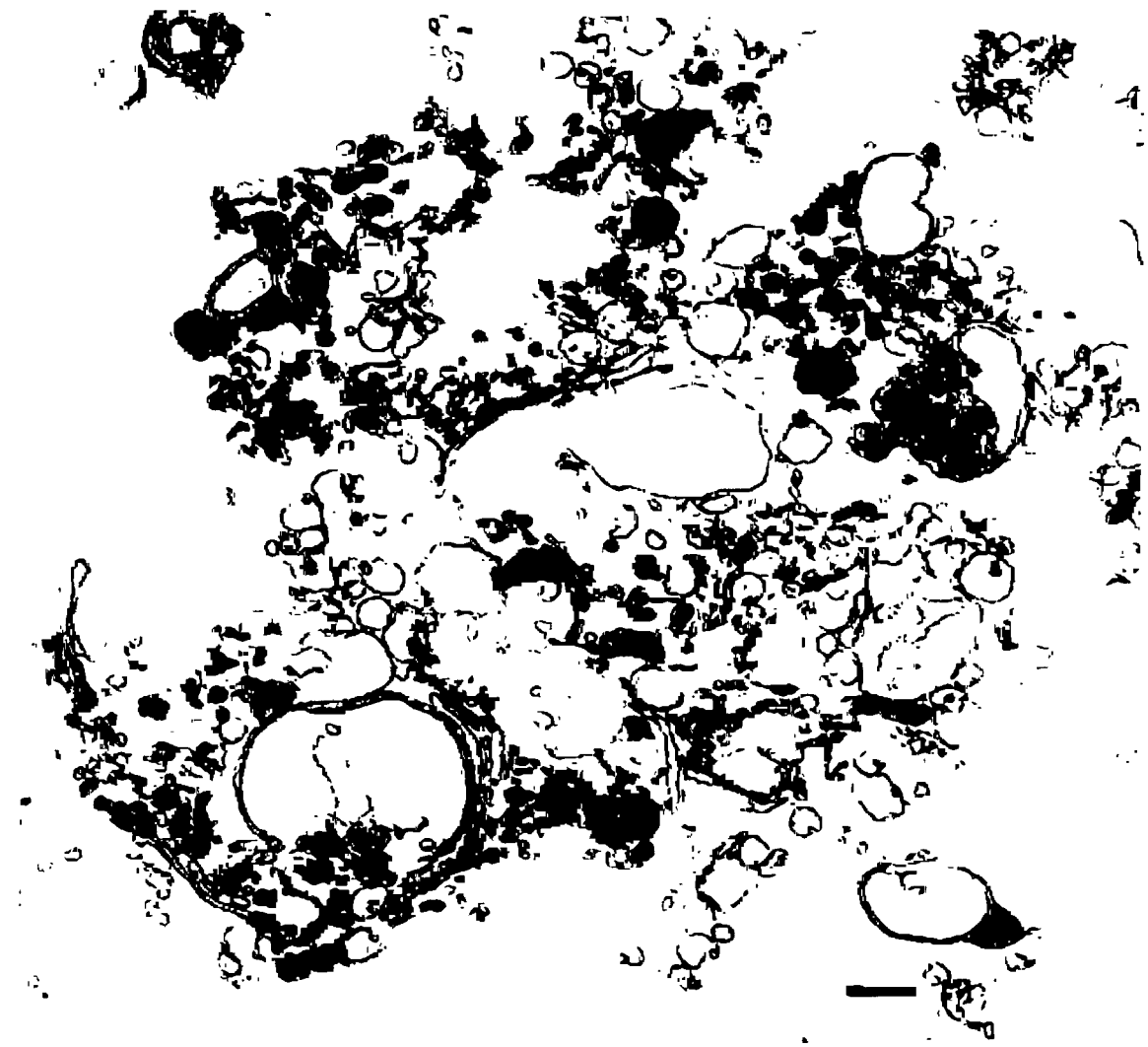
FIG_1

SAMPLES INSERTED

SAMPLES DRAWN ONTO FILTER

DISPENSING PROCESSING
CHEMICALS & INCUBATING

ASPIRATING CHEMICALS
OUT OF APERTURES

DISENGAGING FLUID
TRANSFER PLATE

ENGAGING RETAINER
PLATE

INVERTING PLATE ASSEMBLEY

TRANSFERING SAMPLES FROM MEMBRANE TO WELLS OF RETAINER PLATE WITH PRESSURISED AIR

REMOVING FILTER AND PRESSURE PLATE

ADDING EMBEDDING SOLUTION INTO WELLS

REMOVING EMBEDDED SAMPLES FROM RETAINER PLATE

SLICING EMBEDDED SAMPLES FOR ELECTRON MICROSCOPE EXAMINATION

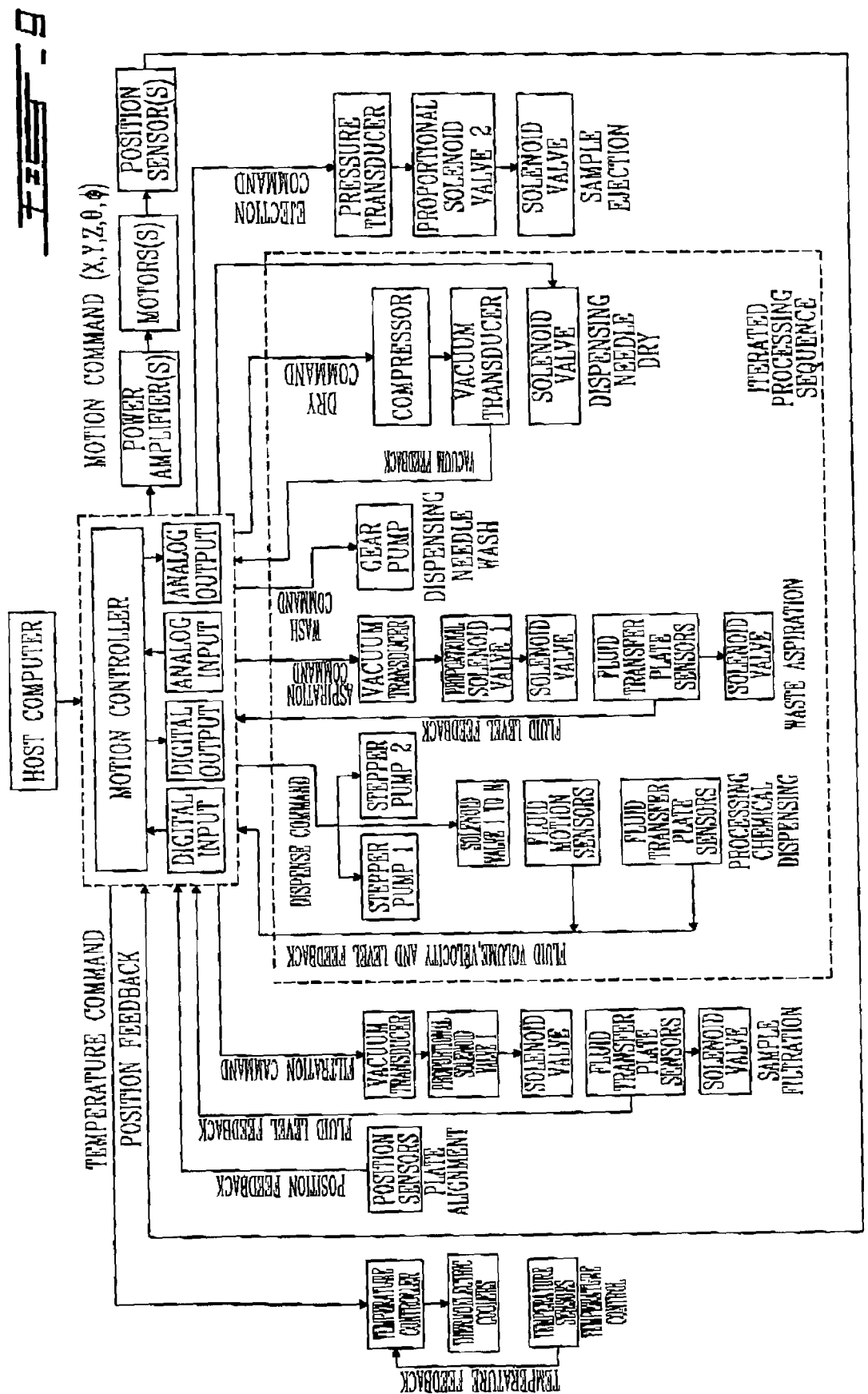

ELECTRON MICROSCOPY CELL FRACTION SAMPLE PREPARATION ROBOT

TECHNICAL FIELD

The present invention relates to a system for the preparation of cell fraction samples for electron microscopy. More particularly, this invention relates to a fully automated, robotically manipulated fluid handling system for temperature controlled, high-throughput parallel preparation of cell fraction samples for electron microscopy.

BACKGROUND OF THE INVENTION

Biomedical research is requiring more specialised equipment expressly suited for the new demands of burgeoning new fields such as large scale proteomics, which require more automated, parallel processing of complex protocols to be accomplished in reasonable time limits. Proteomics, for example, generally involves the systematic separation, identification and characterization of the proteins present in an given sample of tissue or biological fluid at a given time.

Certain processes in proteomics research are currently very time consuming, require individual sample preparation, and do not lend themselves to accurate reproducibility. As more research laboratories are taking on a proteomics approach, there is increasing demand for scaling-up traditionally used bench methodology by implementing robotic systems capable of high-throughput preparation and experimentation processing.

Electron microscopy is often required in proteomics research, especially as proteomics has evolved from a whole cell based approach to an organellar based approach. Using an electron microscope for identification and verification of sub-cellular and protein targets, requires the careful preparation of cell fraction samples to be studied. Electron microscopy is required to validate the purity of the cell fraction sample preparations by morphometry, and to confirm the localization of proteins within isolated organelles.

The currently employed approach for the preparation of cell fraction samples for electron microscopy involves a time consuming, manual methodology including using a filtration apparatus to deposit the sample onto a filtration membrane, and subsequently exposing the sample to a complex protocol of chemical treatments. Cell fraction samples prepared in this way for electron microscopy must be individually prepared, and take approximately 4 days per sample to complete. This process is overly time and labor consuming, and renders any high-throughput processing of samples impossible. FIG. 1 shows an electron micrograph image of such a prepared sample. The scale line represents 240 nanometers.

WO 00/72968 published Dec. 7, 2000, discloses a multiple fluid sample processor and system capable of high through put combinatorial processes, chemical synthesis and diagnostic arrays, and biological assays and processing. A multi-layered fluidic array comprises a plurality of micro-sized reservoirs and interconnecting channels. A pressure or vacuum pumping system is used for fluid delivery and removal. The device can include an upper reservoir layer, a center distribution plate, and a lower well plate, all of which are stacked vertically and can be releasably coupled together. The bottom plate containing the samples process through the other layers, is detachable from the other plates, and conveyed to another location for subsequent processing of the samples. This is preferably done by robotic or other automated means.

SUMMARY OF THE INVENTION

Therefore, there is a need for an automated device capable of high-throughput preparation of cell fraction samples for use in electron microscopy.

It is an object of the present invention to provide an electron microscopy cell fraction sample preparation device capable of reducing preparation times.

It is another object of the present invention to provide a high-throughput cell fraction sample preparation system.

It is a further object of the present invention to provide a device capable of parallel preparation of a plurality of cell fraction samples for electron microscopy.

It is a further object of the present invention to provide an automated method of cell fraction sample preparation.

It is a further object of the present invention to provide a robotic system capable of automated high-throughput, parallel preparation of cell fraction samples for electron microscopy.

Therefore, according to the present invention, there is provided a parallel processing, fluid handling apparatus for concurrent temperature controlled preparation of a plurality of cell fraction samples adapted to be used for electron microscopic viewing, the apparatus comprising: a sample receiving member comprising a plurality of discrete apertures each adapted to receive a biological sample therein; fluid handling means for inserting and removing fluid to and from the plurality of apertures substantially in parallel, permitting the biological samples to be processed substantially in parallel by the insertion and removal of processing fluid; and separation means for the parallel isolated separation of the post-processing samples; whereby the post-processing samples are adapted to be polymerized in embedding solution and removed from the sample receiving member.

Therefore, according to the present invention, there is also provided a parallel processing, fluid handling apparatus for concurrent temperature controlled preparation of a plurality of cell fraction samples for electron microscopy, the apparatus comprising: a filter plate having a major surface and a plurality of apertures extending through the plate in a direction normal to the major surface, and comprising a filter membrane transversely disposed with respect to the apertures and adapted to receive biological samples thereon; a pumping member comprising at least a nozzle, substantially normally directed with respect to a major surface of the pumping member, being in fluid flow communication with the apertures of the filter plate, disposed on a first side of the filter plate, and adapted to provide one of vacuum and pressure to the apertures of the filter plate; a selected one of a fluid transfer plate and a retainer plate; the fluid transfer plate having at least one aperture extending therethrough, the fluid transfer plate being releasably engageable with a second side of the filter plate opposite the first side, such that the at least one apertures in the fluid transfer plate and the filter plate are in fluid flow communication, and the plurality of apertures are discretely sealed to prevent fluid transfer between laterally adjacent apertures, the at least one aperture in the fluid transfer plate and the plurality of apertures of the filter plate being adapted to provide processing fluid reservoirs for each sample; the retainer plate, releasably engageable to the second side of the filter plate and interchangeable with the fluid transfer plate, comprising a removable multiple-well plate engaged therein, the multiple-well plate comprising a plurality of closed bottom wells each adapted to receive polymerized embedding solution therein and corresponding to and being in fluid flow communication with the plurality of apertures of the filter plate; and a biasing mechanism for releasably connecting in sealed engagement, at least one of the fluid transfer plate and the retainer plate, to the filter plate.

There is also provided, in accordance with the present invention, a biasing mechanism for releasably connecting stackable plates of a parallel processing, fluid handling apparatus, the mechanism comprising: a first plate and a second plate adapted to be stacked together, each plate comprising a plurality of corresponding apertures; at least one mechanical alignment member for aligning corresponding apertures in the plates when said plates are stacked together; one of the first plate and the second plate comprising an electromagnetic coupling element, and the other of the first plate and the second plate comprising a magnetic coupling member corresponding to the electromagnetic coupling member, wherein the electromagnetic coupling member and the magnetic coupling member are normally retained together such that the first and second plates are retained together and laterally adjacent apertures are sealed off from each other; and the electromagnetic coupling element being selectively disengageable from the magnetic coupling member when energized, whereby the first and second plates are disengaged from one another.

There is additionally provided, in accordance with the present invention, a method of simultaneously preparing a plurality of cell fraction samples for electron microscopy comprising the steps of: providing a filter plate having a plurality of apertures and comprising a filter membrane for deposit thereon of a sample during processing; providing a fluid transfer plate having at least one aperture, the fluid transfer plate being releasably engageable to the filter plate; providing a pumping member comprising at least a nozzle; engaging the fluid transfer plate to a first side of the filter plate, such that the plurality of apertures and the at least one aperture are substantially aligned and in fluid flow communication with one another, forming a plurality of composite discrete passages in fluid flow communication with the nozzle and having the filter membrane transversely mounted between the plurality of apertures and the nozzle, and each composite discrete passage being sealed off from laterally adjacent passages; inserting a biological sample into the second aperture; providing a vacuum source to the nozzle to draw the samples onto the filter membrane; processing the samples by performing at least one processing cycle, each cycle comprising: dispensing chemicals into the second apertures; incubating the mixture of chemicals and samples; aspirating the chemicals out of the apertures; disengaging the fluid transfer plate from the filter plate, and replacing it with a retainer plate, the retainer plate including a removable multiple-well plate, comprising a plurality of wells having a polyermized embedding solution therein, disposed within the retainer plate such that the plurality of wells are aligned with the plurality of apertures of the filter plate; providing a pressure source to the nozzles to transfer the processed samples from the filter membrane to the polymerized embedding solution; adding further polymerized embedding solution into the plurality of wells to cover the samples; and removing the samples embedded in the polymerized embedding solution from the wells and taking sections of the embedded samples adapted for electron microscope examination.

There is further provided, in accordance with the present invention, a method of simultaneously preparing a plurality of cell fraction samples for electron microscopy comprising the steps of: providing a sample receiving member having a plurality of discretely sealed wells able to concurrently receive therein a biological sample and processing fluid; inserting a biological sample into a plurality of the wells; inserting processing fluid into the plurality of the wells, and processing the samples concurrently by performing at least one fluid exchanging processing cycle; separating processed samples from the processing fluid; embedding the processed samples in an embedding solution; and removing thin sections of the embedded samples for electron microscope examination.

BRIEF DESCRIPTION OF THE DRAWINGS

Further features and advantages of the present invention will become apparent from the following detailed description, taken in combination with the appended drawings, in which;

FIG. 1 is an electron micrograph of a cell fraction sample created using a prior art cell fraction sample preparation process.

FIG. 9 is a control system block diagram for the automation of the full robotic assembly of FIG. 8,

DETAILED DESCRIPTION OF THE PREFERRED EMBODIMENT

Figure 2A:
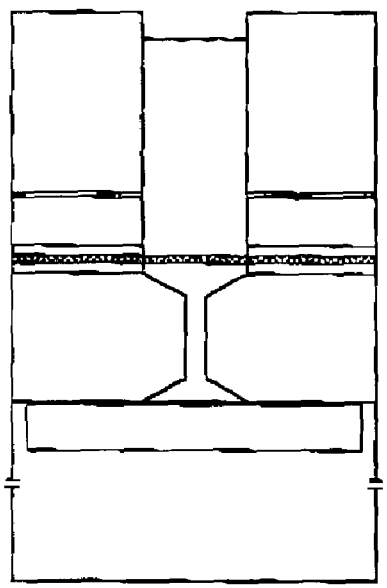
FIGS. 2*a* to 2*m* are schematic cross-sectional views of steps of a method used to create cell fraction samples according to the present invention.
Figure 2B:
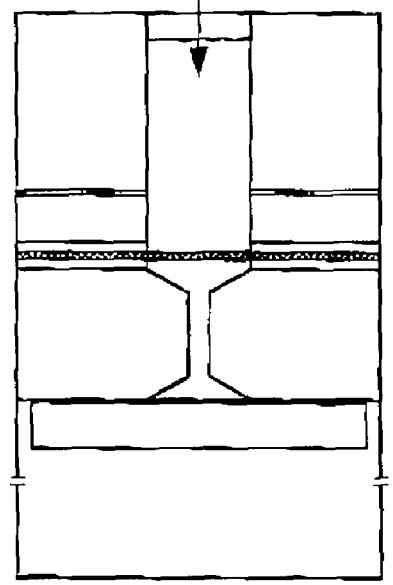
Figure 2C:
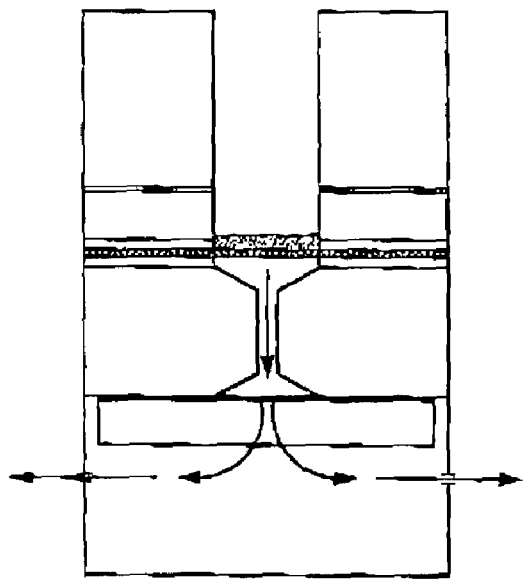
Figure 2D:
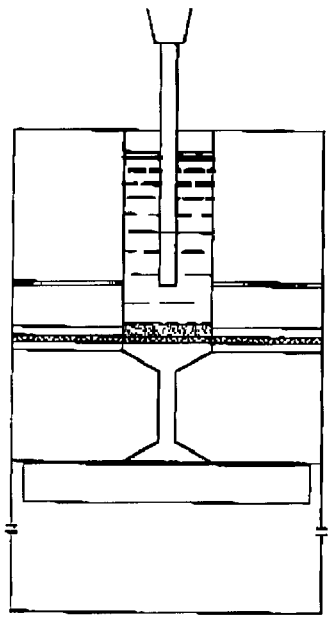
Figure 2E:
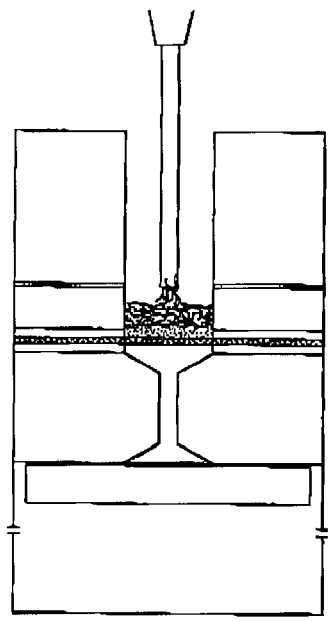
Figure 2F:
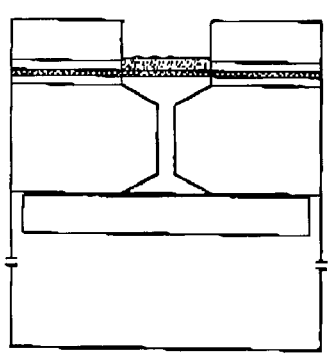
Figure 2G:
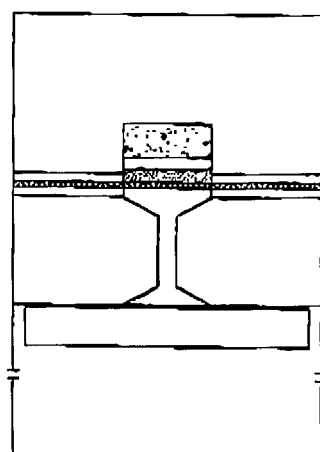
Figure 2H:
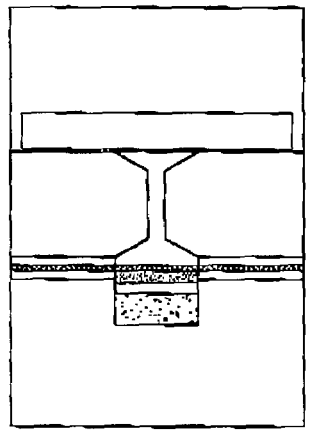
Figure 2I:
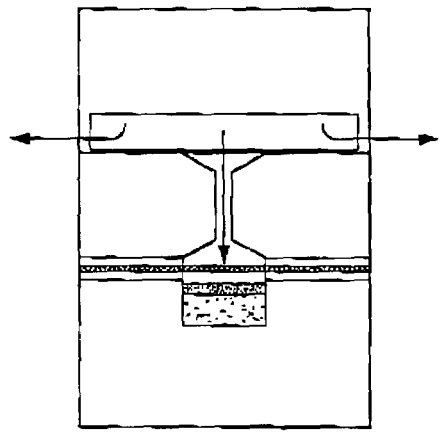
Figure 2J:
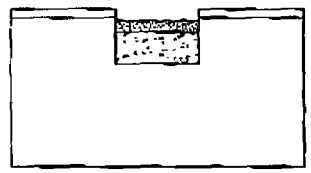
Figure 2K:
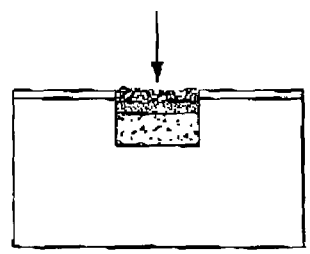
Figure 2L:
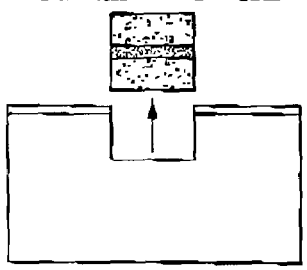
Figure 2M:
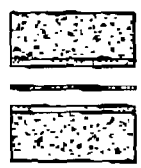

The present apparatus is generally a robotic manipulator and fluid handling system for the fully automated, temperature controlled preparation of a plurality of cell fraction samples for electron microscopic examination. It is capable of preparing a plurality of embedded cell fraction samples at the same time using the full range of preparation protocols. Although the device could be adapted for providing any high-volume, parallel processing, fluid sample preparation and handling, the device is preferably intended for cell fraction sample preparation used in proteomics research for the characterization of isolated organelle purity and location of novel and unexpected proteins by quantitative immuno-labeling. The present device will significantly increase cell fraction sample preparation throughput by a factor of at least 1,000 compared to current manual cell fraction sample techniques. The integrated design of the present invention permits the automation of a significant number of complex protocols while minimizing stress on the samples. It also assures standardized high quality sample preparation for analysis that is not currently available by any other approach.

The increasing scope of proteomics efforts requires laboratories to implement and scale traditional "bench" methods to allow for the high-throughput processing of experimental samples. The present device described below permits a plurality of samples, 96 samples in the preferred embodiment shown and described, to be simultaneously prepared, unattended, in a flexible time limit as short as one working day. This eliminates one of the key bottlenecks in proteomics research and provides, for the first time, a standard of reproducibility in sample preparation and evaluation, hitherto unattained. While the samples can be prepared with the present apparatus in a single day, adjustable parameters allow for processing time to be extended if required.

The automated system of the present invention comprises a core mechanism consisting of four stackable plates, which may be configured in two main configurations for separate chemical processing of up to 96 parallel samples. The modular design of the core mechanism provides the flexibility necessary to automate complex chemical processing protocols as well as integrating with a 5-axis motion control system. The principle components of this core mechanism are illustrated in FIG. 3a through FIG. 7, and described in detail below.

The four principle components of the core mechanism are: a fluid transfer plate 14 providing individual fluid reservoirs for each of the 96 samples, a filter plate assembly 12 holding the filter membrane-bound samples throughout processing, a pumping plate 16 for vacuum filtration of the cell fraction samples onto the filter membrane and pressure delivery of the processed samples with pressurized air and, a retainer plate assembly 18 including a removably engaged 96 well plate comprising a polymerized embedding solution therein for collection of the processed samples at the end of the automated protocol.

Although the pumping plate is described herein as being a discrete member, it is equivalently conceivable that the pressure plate is in fact integrally formed with the pressure plate as a single unit. In such a case, a nozzle or nozzles would be provided within the integral plate to provide pressurized air or a vacuum source to perform substantially the same function as the pumping plate described herein. Similarly, where ever feasible, other plates could be combined to form integral units. For example, if the fluid transfer plate could be combined into the filter plate, or an integral filter/pumping plate. However, this may only function properly if the pumping plate is capable of providing sufficient pressure to transfer the samples from the filter membrane to the embedding solution in the wells of the retainer plate.

Two different configurations of the fluid handling apparatus core mechanism are used throughout the automated sample processing protocol, namely a primary configuration 10a and a final configuration 10b. The primary configuration 10a consists principally of the fluid transfer plate 14, the filter plate assembly 12 and the pumping plate 16. For the final configuration 10b, the fluid transfer plate 14 is interchanged for the retainer plate assembly 18. In both configuration, three plates are held firmly together throughout processing by eight permanent magnets (four per face) built into the filter plate, which is always located in the center of the configuration. All other plates contain corresponding electromagnets for de-coupling of the plates from the central filter plate assembly.

Figure 3A:
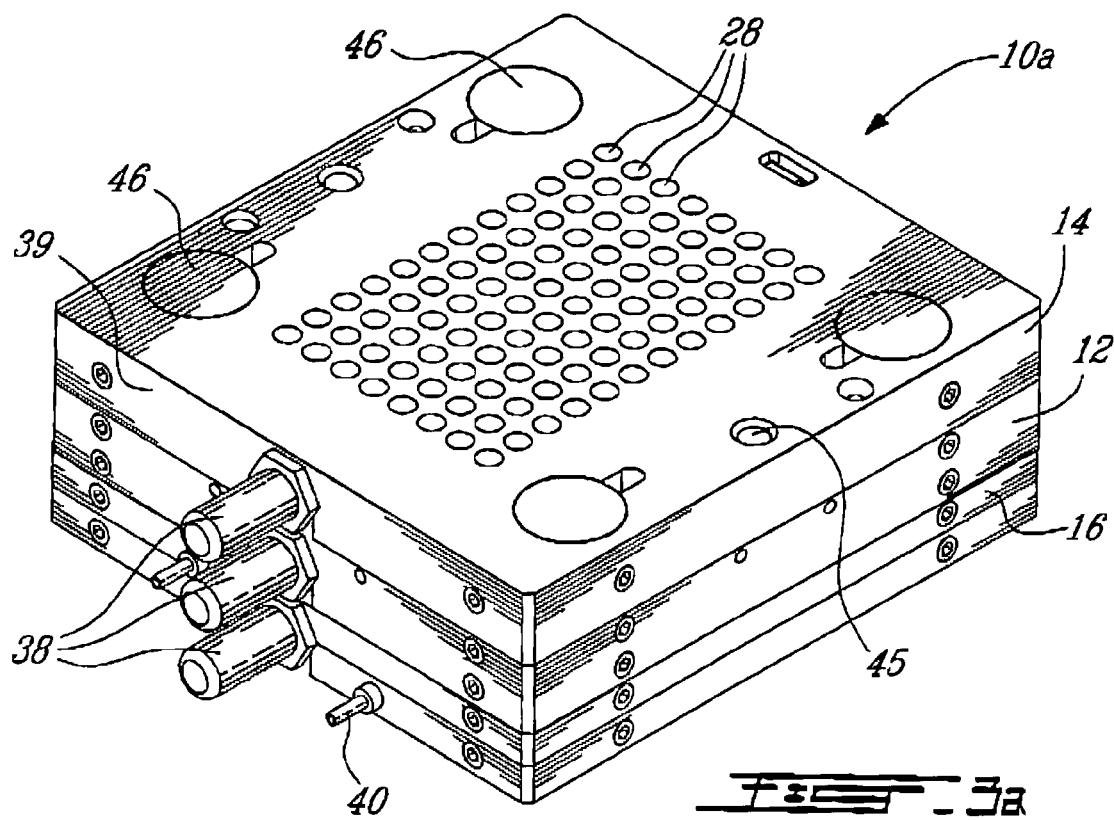
FIG. 3*a* is a perspective view of a primary configuration assembly of the cell fraction preparation apparatus of the present invention.
Figure 3B:
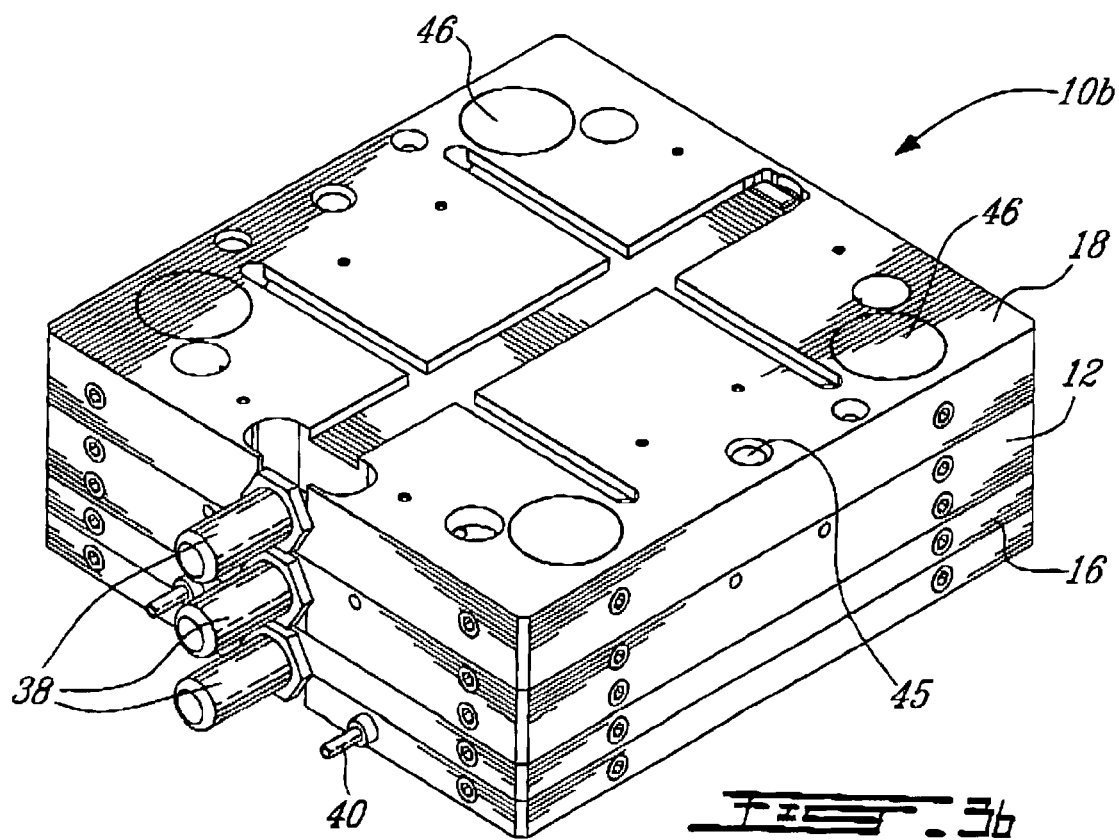
FIG. 3*b* is a perspective view of a final configuration assembly of the cell fraction preparation apparatus of the present invention.

Referring now to FIGS. 3a and 3b which show the primary and final configurations respectively of the core mechanism of the fluid handling apparatus in more detail. The primary configuration 10a of the fluid handling apparatus' core mechanism comprises generally the central filter plate assembly 12 engaged between the upper fluid transfer plate 14 and the lower pumping plate 16. All plates have substantially the same dimensions, and are preferably aligned using mechanical and magnetic alignment members. At least two dowel pins 43 protrude from either side of the filter plate assembly 12, and are adapted to mate with corresponding holes 45 located in all other plates which are engageable with the central filter plate assembly. Any other similarly effective mechanical alignment members can equivalently also be used. Eight electromagnets 46, four located on each major surface of the fluid transfer plate 14, the pumping plate 16 and the retainer plate assembly 18 are magnetically engageable with the permanent magnets 44 disposed within the filter plate assembly, and shown in more detail in FIG. 5. Further, all plates can additionally comprise proximity sensors, preferably magnetic ones, embedded therein, which signal proper alignment to a robotic motion controller. All stackable plates have a connector 38 protruding from a common members 38 provide a connector for plugging an electrical connection thereto. This provides the necessary signal and power connections for any sensors and switches in each plate. The final configuration 10b of the core mechanism of the fluid handling apparatus is similar to the primary configuration, with the exception of the interchange of the fluid transfer plate for the retainer plate assembly 18.

Figure 4:
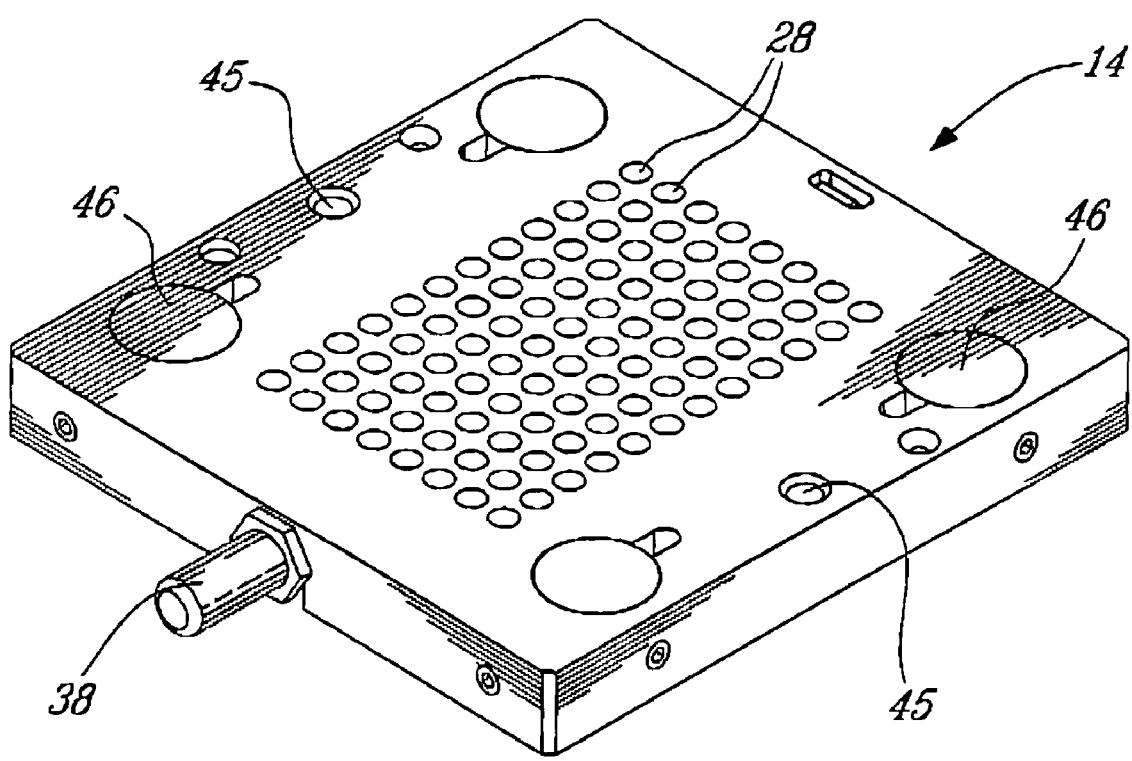
FIG. 4 is a perspective view of a fluid transfer plate of the primary configuration assembly of FIG. 1*a*.

Referring to FIG. 4, a plurality of apertures 28, numbering preferably ninety-six in the embodiment shown and described herein, are transversely located in the fluid transfer plate 14. The apertures 28 extend through the thickness of the plate. The apertures 28 provide individual fluid reservoirs for each of the ninety-six samples during chemical processing of the samples. The fluid transfer plate 14 additionally comprises embedded sensors for independently detecting and monitoring the fluid levels in all individual fluid reservoirs formed by the apertures 28. When the fluid reservoirs can therefore be filled until the fluid level sensors in each reservoir indicate that a predetermined desire level has been reach, at which point no further fluid is added. The fluid transfer plate comprises four electromagnets 46, adapted to correspond to the four permanent magnets 44 disposed on a first surface 48 of the filter plate assembly. The faces of the electromagnets 46 are located on the lower surface, not visible in FIG. 4, of the fluid transfer plate that is to be mated to the filter plate.

Figure 5:
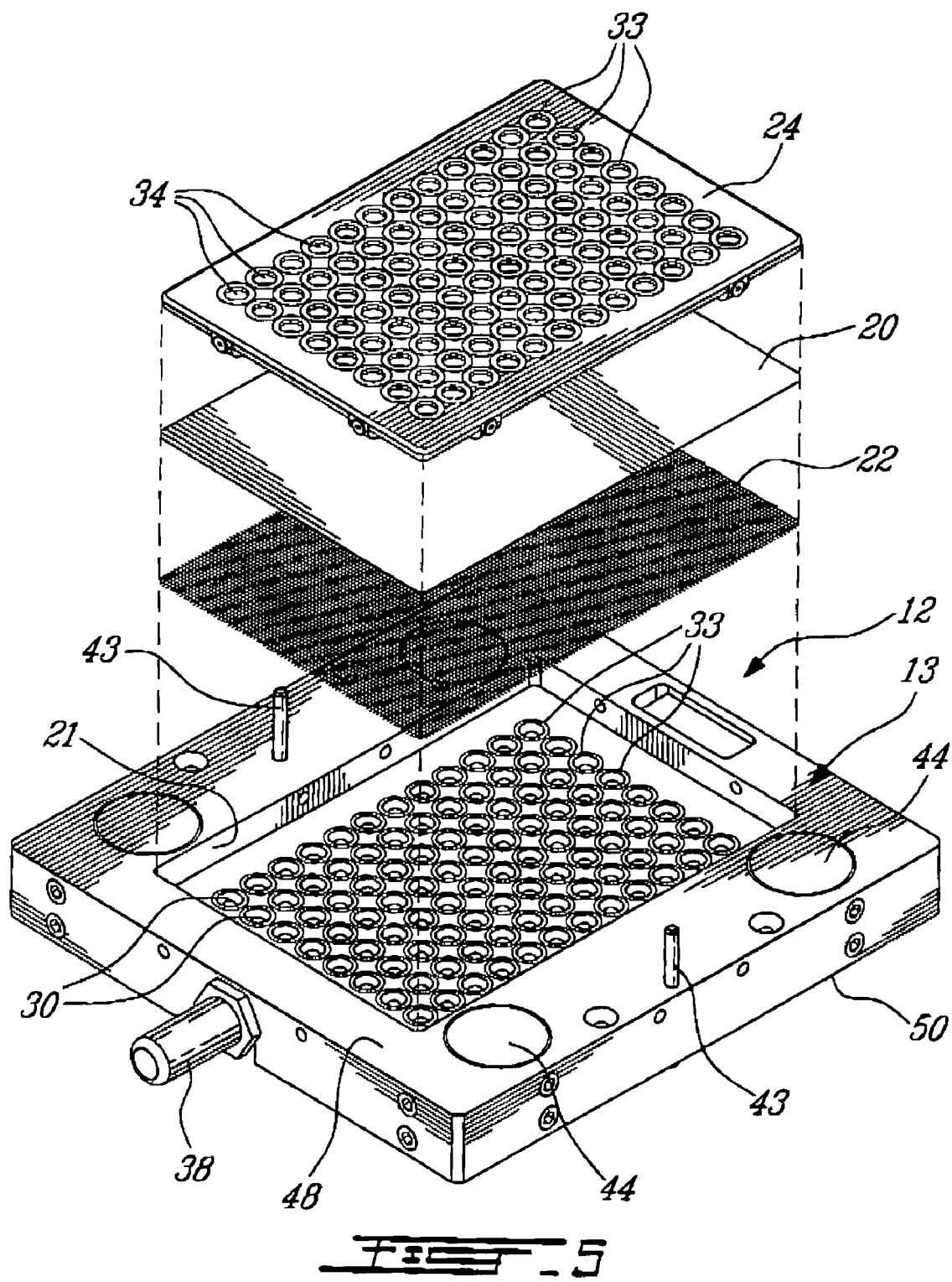
FIG. 5 is an exploded perspective view of a filter plate assembly of the cell fraction preparation apparatus of FIGS. 3*a* and 3*b*.

The filter plate assembly 12 in FIG. 5 comprises a filter plate base member 13, having a central rectangular recess 21 for receiving therein a filter membrane 20, filter plate screen 22 and filter plate cap 24. The filter plate base member 13 preferably comprises ninety-six transversely extending apertures 30 therein, corresponding to and adapted to be aligned with the apertures 28 of the superimposable fluid transfer plate 14. Both the apertures 30 and the apertures 34 of the filter plate cap are formed such that O-rings 33 can be added around each aperture. The filter plate cap 24 preferably has O-rings 33 around each aperture 34 on both the top and bottom surfaces of the cap. All O-rings 33 can be standard O-rings having circular cross-sections. When two layers of O-rings are to be superimposed, such as for examples those sealing each aperture 30 of the filter plate base member 13 and those on the underside of the filter plate cap, which are to mate to provide sealing with only the filter membrane 20 and the filter plate screen 22 therebetween, one set of O-rings preferably is a so called X O-ring, having a generally X-shaped cross-sectional area and are particularly adapted for mating with standard O-rings. All O-rings 33, just like all components of the entire present cell fraction preparation apparatus, can be autoclaved for sterilization. Corresponding apertures 32 and 34 in the filter plate screen 22 and filter plate cap 24, also are aligned with the main apertures 30, normally directed with respect to the major surface 48 of the filter plate member 13, when the filter plate screen 22 and filter plate cap 24 are disposed within the recess 21 of the filter plate base member 13. The filter membrane 20 extends between the base member 13 and the filter plate screen and filter plate cap, such that when the filter plate assembly 12 is assembled, the plurality of individual samples can be deposited on the filter membrane, without being intermixed with adjacent chemically processed samples. Teflon seals between each element of the filter plate assembly, and between each stacked plate, are preferably used to ensure that each composite fluid passage is well sealed from adjacent passages. Eight permanent magnets, four on the first major surface 48 and four on the opposing major surface 50 of the filter plate member 13, are used to magnetically engage the other stackable plates to the central filter plate assembly 12.

Figure 6:
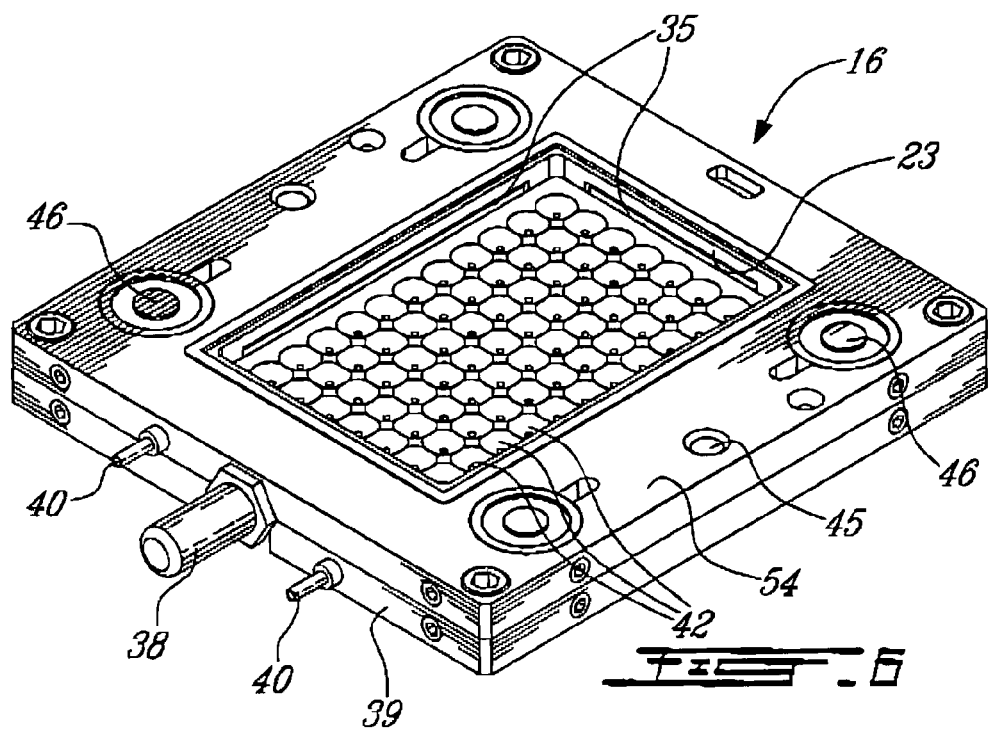
FIG. 6 is a perspective view of a pumping plate of the cell fraction preparation apparatus of FIGS. 1*a* and 1*b*.

Referring now to FIG. 6, the pumping plate 16 can be alternately used as a pressure or vacuum producing member of the fluid handling core mechanism. Specifically, when the core mechanism is in the primary configuration 10a, the pumping plate 16 is used as a vacuum source to draw the samples onto the filter membrane 20 retained within the filter plate assembly 12. When the core mechanism is in the final configuration 10b, wherein the fluid transfer plate is replaced with the retainer plate assembly, the pumping plate 16 is used as an air pressure source to transfer the processed samples from the filter membrane 20 to the embedding solution contained within the retainer place assembly 18. The pumping plate 16 preferably comprises two sets of nozzles, a plurality of vacuum nozzles 42 and four side slot pressure nozzles 35, all of which are disposed within a rectangular recess 23 in a first surface 54 of the pumping plate 16. While a plurality of vacuum nozzles 42 are used, preferably numbering seventy-seven arranged in a 7×11 matrix such that each nozzle lies between the apertures in the filter plate which preferably number 96 in an 8×12 matrix, fewer or even a single nozzle could also theoretically equivalently be used, in order to provide vacuum and pressurized air to the apertures. The nozzles 42 are internally in fluid flow communication with one of the hose attachments 40, particularly the lower one shown in FIG. 6, protruding from the same edge surface 39 from which the connector 38 extends. The hose attachments 40, provide inlet and outlet feed passages for the pumping plate, such that either a pressure or vacuum source can be engaged thereto. A pressurized fluid, preferably air, is provided from the side slot nozzles 35, perpendicularly directed with respect to the vacuum nozzles 42. Vacuum nozzles 42 within the central pumping plate recess 23, permit fluid flow communication between the vacuum house attachment and the recess 23, and consequently between the vacuum source and the apertures of the filter plate. Four electromagnets 46 are disposed within the pumping plate on the major surface 54, adapted to correspond to the location of the permanent magnets 44 of the central filter plate assembly 12, such that the pumping plate can be releasably engaged to the second surface 50 of the filter plate.

All electromagnets 46 of the plates engageable with the filter plate are oriented such that they are normally magnetically attracted to the permanent magnets 44. This permits the plates to be retained together once stacked, forming a secure separable engagement which prevents the plates from being unexpectedly separated, offer the necessary compression to sufficiently seal the superimposed apertures, and also prevents any fluid flow communication between horizontally adjacent fluid passages by maintaining a seal between the mating flat major surfaces of contiguous plates. When the individually controllable electromagnets 46 on each plate adapted to be engaged to the central filter plate assembly 12 are energized, the energized electromagnets counteract the magnetic attractive force between the permanent magnets and the preferably ferrous electromagnets, causing the plates having the energized electromagnets to be disengageable from the central filter plate. This permits the plates to be normally securely retained together, until such time as one plate, such as the fluid transfer plate, is to be disengaged, in which case all that is required is to energize the electromagnets disposed within the fluid transfer plate, causing said plate to be freely disengageable and even slightly repelled from the central filter plate. The inverse procedure is equally possible for the attachment of a plate to the filter plate.

Figure 7:
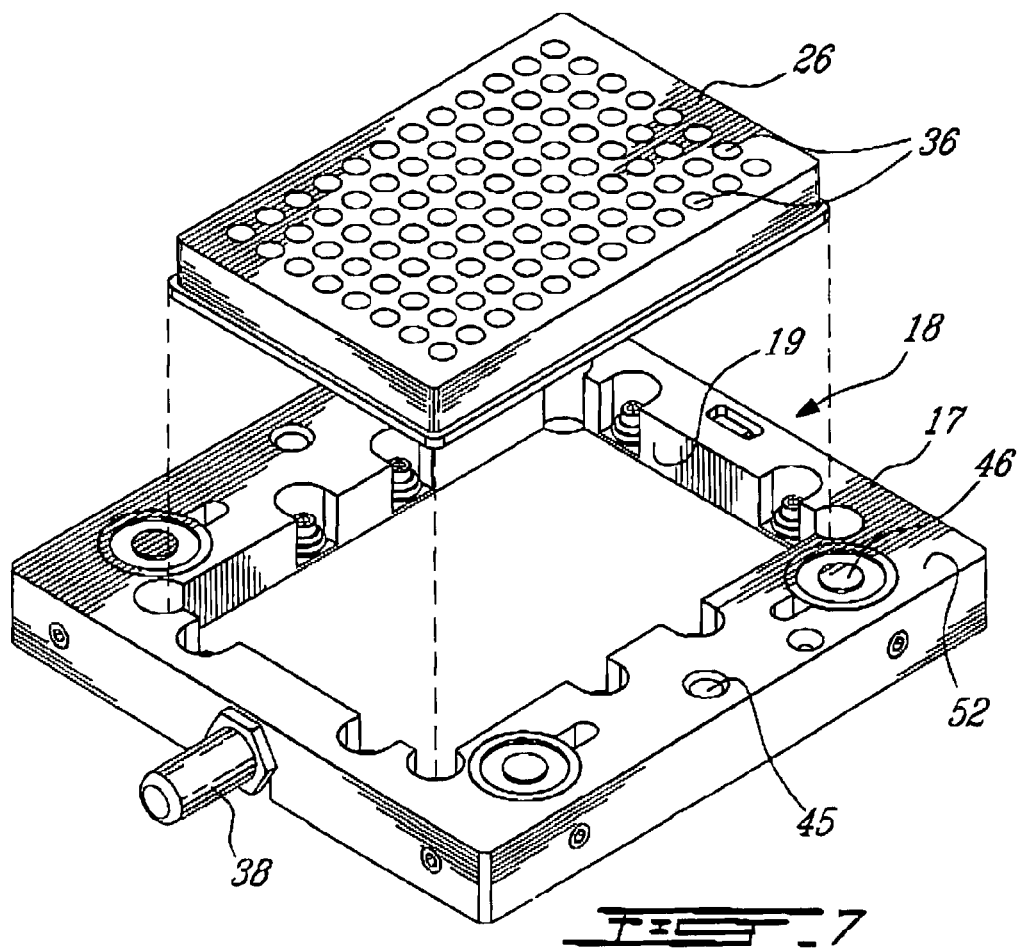
FIG. 7 is a perspective view of a retainer plate of the final configuration assembly of FIG. 1*b*.

The retainer plate assembly 18 shown in FIG. 7 comprises a retainer plate base member 17 having a central rectangular recess 19 formed therein and sized for receiving a multiple-well plate 26. The multiple-well plate, such as a standard 96-well plate, comprises closed bottom apertures 36 which align with and correspond to the apertures 30 of the filter plate assembly 12. The 96-well plate 26 can be securely retained in the recess 19, such that the retainer plate assembly 18 can be inverted without the well plate falling out. The retainer plate comprises rubber grommet assemblies disposed about the edge of the recess 19, preferably two along each edge, frictionally engage the edges of the 96-well plate 26 to ensure that it is securely retained within the recess 19. In similar fashion with the other outer plates adapted for engagement with the central filter plate 12, the retainer plate base member 17 comprises alignment holes 45 for receiving the locating dowel pins 43 of the filter plate assembly, connector 38 and electromagnets 46 on surface 52 for magnetic releasable engagement with the central filter plate.

Having described the principal elements of the core mechanism of the fluid handling apparatus, the methodology involved for the parallel preparation of cell fraction samples using the elements of the core mechanism will now be outlined.

Beginning with the primary stacked plate configuration 10a, biological samples are placed, either manually or by an equivalent automated system, into the individual apertures 28 of the fluid transfer plate 14 of the coupled configuration, using a standard pipette needle for example. The samples can be added into the apertures individually, or in groups of as few as two samples to as many as the number of apertures in the plate. All subsequent manipulations in the processing protocol can be fully automated using a robot as further described below, however the sample processing protocols can equally be manually performed. The process begins by filtering the cellular fraction samples onto the filter membrane 20, by providing a vacuum from the nozzles 42 of the pumping plate 16 produced by the source engaged to the hose attachments 40. Needle manifolds 74 of the robot arm assembly 72, preferably comprising multi-channels as described in further detail below however they can have as few as a single needle, dispense and aspirate processing chemicals to and from the 96 individual composite fluid reservoirs formed above the filter membrane as required by a known protocol for the preparation of cellular fractions for electron microscopy. Table 1 and Table 2 below outline a sample process protocol, used for with the present invention for the automated preparation of cell fraction samples.

During the sample processing performed by such a protocol, the samples and the entire core mechanism is maintained at approximately 4° C. by a thermoelectrically cooled platform 70, which incubates the samples in the processing chemicals. The ability to accurately control the temperature of the entire core mechanism and consequently the samples, is an important feature of the present invention. The thermoelectric platform 70 also permits significant temperature variation, being adjustable such that a temperature range of approximately 4° C.–37° C. is possible. Preferably a temperature range of 2 to 10° C. is most often used. Cyclic oscillation between various temperatures is equally possible. The cycle of dispensing chemicals, incubation, and aspiration of chemicals is repeated as many times as required to complete the protocol.

TABLE 1

Protocols for automated preparation of cellular fractions for electron microscopy. Unless indicated, all manipulations are completed at 4° C.. Repeated steps $N_n$ and respective time durations $T_n$ are specified by the operator. Typical total run times range from 8 to 24 hours for completion.

Fixation (manual steps):

1. Fixation solution contains: 5% glutaraldehyde, 1 mM cacodylate buffer, pH 7.4 and, 0.1% $CaCl_2$.
2. Add an equal volume of fixative to 2 ml of 100 µg/ml membrane protein and leave overnight.
3. Load 400 to 500 µl of fixed cell fraction samples to each well of the fluid transfer plate.

Fixation (automated steps):

1. Filter on Millipore ™ filter type HA 0.45 µm or 0.8 µm.
2. Wash the filter $N_1$ times for time $T_1$ and incubate with 100 mM cacodylate buffer, pH 7.4.

Post fixation: (follow one procedure)

Procedure I:

1.1 Fix the samples in 2% reduced $OsO_4$ in 100 mM cacodylate buffer, pH 7.4 $N_2$ times and incubate for time $T_2$.
1.2 Wash $N_3$ times and incubate each for time $T_3$ with 0.25M sucrose cacodylate buffer.
1.3 Rinse $N_4$ times and incubate each for time $T_4$ with 0.1M maleate buffer, pH 5.7.
1.4 Incubate $N_5$ times each for time $T_5$ in 6% uranyl acetate 100 mM maleate buffer, pH 5.7.
1.5 Wash $N_6$ each for time $T_6$ with maleate buffer
1.6 Wash $N_7$ times each for time $T_7$ with cacodylate buffer.

Procedure II:

2.1 Incubate $N_8$ each for time $T_8$ in 1% tannic acid in cacodylate.
2.2 Wash $N_9$ times and incubate each for time $T_9$ with 1% sodium sulfate in 100 mM cacodylate.
2.3 Incubate $N_{10}$ times and incubate each for time $T_{10}$ in 5% uranyl acetate, 100 mM maleate buffer, pH 5.7.
2.4 Wash $N_{11}$ times and incubate each for time $T_{11}$ with maleate buffer.
2.5 Wash $N_{12}$ times and incubate each for time $T_{12}$ with cacodylate buffer.

Dehydration:

1. Wash with 50% ethanol $N_{13}$ times and incubate each for time $T_{13}$.
2. Wash with 70% ethanol $N_{14}$ times and incubate each for time $T_{14}$.
3. Wash with 90% ethanol $N_{15}$ times and incubate each for time $T_{15}$.
4. Wash with 95% ethanol $N_{16}$ times and incubate each for time $T_{16}$.
5. Wash with 100% ethanol $N_{17}$ times and incubate each for time $T_{17}$.
6. Wash with Propylene oxide for $N_{18}$ times and incubate each for time $T_{18}$.
7. Wash with 1:3 Epon:propylene oxide $N_{19}$ times and incubate each for time $T_{19}$.
8. Wash with 1:1 Epon:propylene oxide $N_{20}$ times and incubate each for time $T_{20}$.
9. Transfer to preembed block.
10. Incubate with 100% Epon for time $T_{21}$.
11. Polymerize.

TABLE 2

Protocol for automated pre-immunolabeling cellular fractions for electron microscopy. Unless indicated, all manipulations are completed at 4° C.. Repeated steps $N_n$ and respective time durations $T_n$ are specified by the operator. Typical total run times range from 8 to 24 hours for completion.

Light fixation (manual steps):

1. Fixation solution contains: 0.05% glutaraldehyde, 0.1M cacodylate buffer, pH 7.4.
2. Add the fixative to the pellet (after incubation of cellular fractions with antibody and centrifugation) of 300 µg membrane protein. Mix gently and leave for 30 minutes.
3. Load 400 to 500 µl of fixed cell fraction samples to each well of the fluid transfer plate.

Light fixation (automated steps):

1. Filter on Millipore ™ filter type HA 0.45 µm with saline solution (10 mM TRIS, 0.9% NaCl, pH 7.4).
2. Wash the filter $N_1$ times for time $T_1$ with saline solution.

Pre-incubation:

1. Wash the filter $N_2$ times for time $T_2$ with 3% BSA/saline solution at 25° C..

Gold-complex incubation:

1. Add the gold-complex (0.5 nm) to the samples for time $T_3$ at 25° C..
2. Wash $N_4$ times for time $T_4$ with saline solution.

Fixation:

1. Fix the samples $N_5$ times for time $T_5$ in 2.5% glutaraldehyde, 0.1M cacodylate buffer, pH 7.4.
2. Wash $N_6$ times for time $T_6$ with 0.1M cacodylate buffer, pH 7.4.
3. Post-fix the samples $N_7$ times for time $T_7$ in 1% reduced $OsO_4$ and 1.5% potassium ferrocyanide.
4. Wash $N_8$ times for time $T_8$ with 0.05M maleate buffer, pH 6.0.
5. Incubate $N_9$ times for time $T_9$ in 2% uranyl acetate and 0.0125M maleate buffer, pH 4.2.
6. Wash $N_{10}$ times for time $T_{10}$ with 0.05M maleate buffer, pH 6.0.

Dehydration:

1. Wash $N_{11}$ times for time $T_{11}$ with 75% ethanol.
2. Wash $N_{12}$ times for time $T_{12}$ with 95% ethanol.
3. Wash $N_{13}$ times for time $T_{13}$ with 100% ethanol.
4. Wash $N_{14}$ times for time $T_{14}$ with propylene oxide.
5. Wash $N_{15}$ times for time $T_{15}$ with 1:1 Epon:propylene oxide.
6. Transfer to preembed block.
7. Incubate with 100% Epon for $T_{16}$.
8. Polymerize.

Once the sample processing protocols have been completed using the core mechanism in the primary configuration 10a, the top fluid transfer plate 14 is electromagnetically released from engagement with the filter plate assembly 12, and is then removed and replaced with the retainer plate assembly 18, inverted such that the wells 36 of the ninety-six well plate 26 are open to and aligned with the apertures 34 of the filter plate cap 24. The retainer plate assembly 18 can then similarly be magnetically engaged to the filter plate assembly, securing it in place. The entire core mechanism assembly in the final configuration 10b, is preferably then rotated 180 degrees as a unit, preferably about a central axis of the filter plate, such that the retainer plate assembly 18 becomes the bottom-most plate, and both the central filter plate assembly 12 and the pumping plate 16 are inverted. The final configuration of three plates is used for delivery of the processed samples to the ninety-six well plate 26 containing the embedding compound, such as polymerized Epon. The samples are transferred from the inverted filter membrane 20 to the wells 36 containing the polymerized embedding solution, using pressurized air provided by the side slot nozzles 35 of the pumping plate 16. The plates are electromagnetically de-coupled and the pumping plate and the filter plate are removed. An embedding solution can then be added to all the open apertures of the retainer plate, in order to seal the processed sample between layers of embedding solution. Finally, once the top layer has been polymerized, the ninety-six well plate 26 containing the individual processed cell fraction samples can be removed from the retainer plate assembly 18, such that the individual processed samples contained in the embedding solution can be removed, sectioned, and prepared as required for viewing under an electron microscope.

As mentioned above, while the previously described protocols and plate manipulations can be manually performed, the present invention provides a preferable, fully automated robot capable of performing the entire process once the initial biological samples are inserted into the reservoirs defined by the apertures of the fluid transfer and filter plates.

Figure 8:
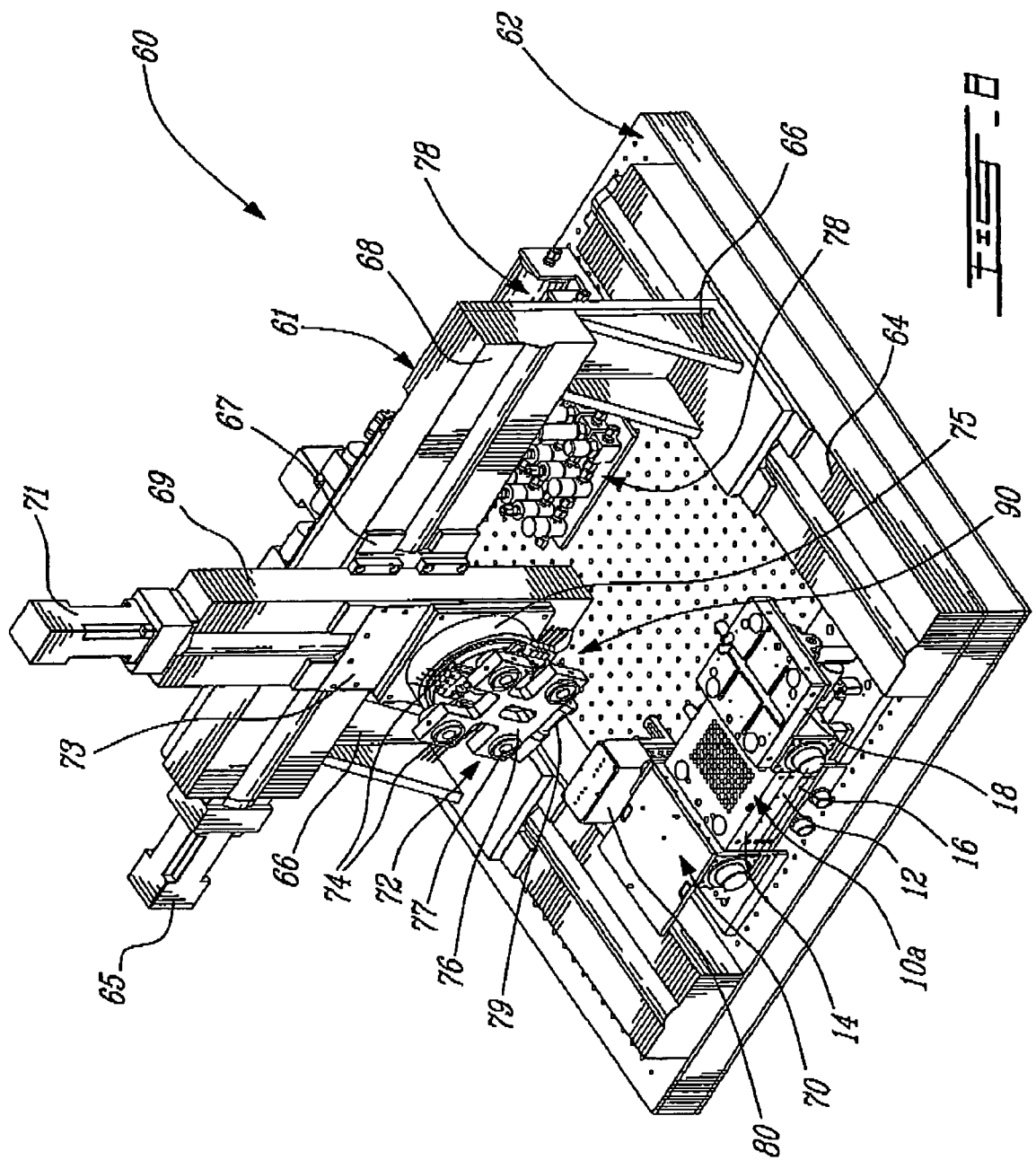
FIG. 8 is a perspective view of a full robotic assembly for the cell fraction preparation apparatus of the present invention.

Referring to FIG. 8, the fully automated robot assembly 60 comprises principally an electromagnetic robot arm assembly 72, a five-axis motion control system assembly 61, the cooling platform assembly 70 adapted to receive the elements of the core mechanism forming the primary and final plate configurations 10a and 10b, and at least one fluids panel assembly 78, all mounted on an underlying base member 62. Preferably a second fluids panel assembly is also used, fixed to the back side of the rail 68. In which case the first fluids panel assembly provides largely air, and the second largely the process liquids. The robot arm assembly 72, which is actuated to permit 90° rotation relative to the rotary table member 75 for convenience, providing the fifth degree of freedom of the five-axis motion control system that would otherwise have four-axis motion control. The robot arm assembly 72 comprises a fluid handling means 90 including at least one needle manifold 74, the fluid handling means 90 being for dispensing and aspirating processing fluids into the apertures 28 of the fluid transfer plate for processing of the samples contained on filter membrane. The robot arm assembly 72 also comprises an electromagnetic plate manipulating member 76 having electromagnets 77 thereon, which is capable of grasping and releasing the elements of the stacked plate fluid handling apparatus described above, such that it is adapted for interchanging the fluid transfer plate 14 with the retainer plate assembly 18, for rotating the entire stacked plate assembly about a central axis such that the plates of the final configuration 10b are inverted, and for removing the filter plate assembly and the pumping plate from the retainer plate assembly at the end of the cell fraction sample preparation procedure, such that the ninety-six well plate 26 can be removed from the retainer plate assembly 18. Adjacent the thermoelectrically cooled platform assembly 70 for incubating the samples in the processing chemicals during the sample processing protocol, is engaged a wash station 80, adapted for cleaning the interior and exterior surfaces of the individual dispensing/aspiration needles of the needle manifold assemblies 74, which can aspirate water to ensure an even more thorough wash.

The electromagnetic robot arm assembly 72 is displaceable and is controlled by the four-axis motion control system 61, comprising two horizontal base rails 64 on which slide mobile supports 66 for an upper transverse horizontal table 68, a carriage 67 horizontally displaceable on the upper transverse table 68 and which retains a vertical table 69 for vertical relative motion therewith, and a rotary table mounting bracket 73 that is vertically displaceable on the vertical table 69 and comprises a rotary table member 75, which retains the robot arm assembly 72 and permits the pivotal motion of the robot arm about a horizontally extending center axis at the center of the rotary table member 75. Actuating input member 65 of the upper transverse horizontal table 68 and actuating input member 71 of the vertical table 69, are adapted for moving their respective tables in space, such that coupled X-Y-Z axis motion of the robot arm assembly 72 is provided. The further coupled θ-axis rotational motion of the robot arm assembly about the rotating table 75, coupled to the Z-axis, creates four-axis motion control for the robot arm assembly 72 of the fully automated robot 60.

The robot arm assembly 72 preferably also has an actuated hinging mechanism 79 enabling Φ-axis rotation of the electromagnetic plate engaging member 76, thereby being displaceable from a normally vertical position substantially parallel to the rotary table mounting bracket 73 to a horizontal position substantially perpendicular therefrom. This enables the electromagnets 77 of the robot arm assembly 72 to be engageable with the magnets on the plates of the core fluid handling mechanism, in order to be capable of manipulating one or several of the plates. Generally, the robot arm assembly 72 is used in the vertical position when dispensing and aspirating processing fluids, and is used in the horizontal position for plate or plate assembly manipulation. This last rotational axis motion completes the five-axis motion of the entire robot control system.

The fluids panel assembly 78 that is provided on the base 62 of the robot 60, and the similar fluid panel assembly included on the reverse of the transverse table 68, can include a plurality of fluid containers, pumps, valves adapted to contain, mix, and supply the air and processing chemicals as required by the sample processing protocols used. As mentioned above, the panel 78 is generally used for the air, and the other fluids panel mounted directly on the moving transverse table, is used for all the processing fluids. Conduits (not shown) ensure fluid flow communication between the fluids panel assembly 78 and the needle manifold assemblies 74 of the robot arm assembly 72, such that the necessary processing chemicals can be fed to and received from the individual plate aperture engaging needles.

FIG. 9 outlines, in block diagram form, the preferred automation controlled processes of the fully automated robot assembly 60 described above. The parameters for the processes (e.g.: number of iterations and time duration) are initially set by the operator on the host computer and then downloaded to the motion controller. All subsequent events are driven by the motion controller and its associated digital and analog input/output controls.

There are two levels of control to assure maintenance of sample integrity during automated sample filtration. A vacuum transducer is used to indicate adjustment of a vacuum source flow rate through the pumping plate by way of a proportional solenoid valve. This allows for gentle filtration of the samples. Because the vacuum source is used for several processes, the flow is gated through a direct-acting solenoid valve as well. Additionally, as the cell fraction suspensions are filtered down onto the charged filter membrane, sensors embedded into the fluid transfer plate indicate the individual fluid levels (up to 96) to the motion controller. If the fluid levels are not similar, the motion controller dictates motion control steps to dispense additional buffer into those wells filtering more quickly than the others and try to proceed. If there is repeated failure, the system stalls to allow manual inspection of the problem.

Processing chemicals are dispensed to the samples via two stepper pumps and several banks of solenoid valves that act as gates to the individual reservoirs of the processing chemicals. Several chemicals are dispensed as progressive proportions of two of the chemicals. Therefore, two pumps and two solenoid valves are actuated simultaneously to mix the two chemicals. As the processing chemicals are being dispensed, there are two levels of control to ensure proper operation of the fluids handling and integrity of the samples. In the first, as fluid is pumped toward the dispensing needles, fluid motion sensors (IR sensors) detect the presence and velocity of the fluid. The motion controller can calculate volume as a check on the system as the geometry of the fluid lines is know. In the second level of fluid handling control, as the fluid is dispensed into the wells of the fluid transfer plate, sensors embedded in the fluid transfer plate indicate to the motion controller whether the appropriate level of fluid in the individual wells has been attained. The process is repeated for as many times it takes to iterate through the sample processing loop of chemical dispensing and aspiration and the cycle of needle washing and drying.

All automated events except for temperature control are preferably nested within the motion control protocol. The temperature of the four plates is maintained with temperature sensors and thermoelectric coolers located in the walls of the cooling platform. The temperature control operates semi-independently from the motion controller and its associated input/output controls. Signals from the motion controller dictate the "on/off" state of temperature control when the whole robot powered on or off. If the operator dictates that the temperature must change during some portion of the sample processing protocol, the motion controller will deliver a signal to the temperature controller to go to a new temperature set point. Otherwise, the temperature control feedback loop is independent of the motion control loop and any other actuation dictated by the motion controller.

The other control loops indicated within the block diagram indicate that all controlled processes but temperature are nested within the control loop for robotic motion. Furthermore, the events that take place on an iterated schedule for progressive processing of the samples (processing chemical dispensing, waste aspiration, dispensing needle wash, and dispensing needle dry), are enclosed with the dotted line indicated by "Iterated Processing Sequence". All other elements, such as plate alignment and sample filtration, occur one time within a sample processing run.

When spent processing chemicals are removed from the individual wells by way of the aspiration needles, there are two levels of control to assure maintenance of sample integrity during this waste aspiration. A vacuum transducer is used to indicate adjustment of a vacuum source flow rate through the aspiration needle lines by way of a proportional solenoid valve. This avoids aspirating the sample itself. As the vacuum source is used for several processes, the flow is gated through a direct-acting solenoid valve as well. Additionally, as the spent chemical is removed, sensors embedded into the fluid transfer plate indicate the individual fluid levels (up to 96) to the motion controller. If the fluid levels become low, the motion controller dictates motion control steps to stop aspiration from the well(s) and proceed to the following steps.

After dispensing or aspiration of fluids from the wells of the fluid transfer plate, the exterior surfaces of the needles can be cleaned in the wash station. When the needles are to be washed, the motion controller actuates a small gear pump to replenish the gravity overflow section of the wash station with clean water. The duration of the actuation is dictated by the operator before the processing run begins. In order to remove any excess water droplets from the exterior surfaces of the needles following a wash, the robot delivers the needles to the wash stations drying section. Here, the vacuum source line is opened fully to creates an abrupt pressure drop and carry the moisture on the needles away to the waste. A compressor builds the appropriate level of vacuum as indicated by a vacuum transducer (located on the vacuum reservoir). The actuation is completed by actuation of a solenoid valve by the motion controller.

Sample ejection is accomplished by slowly pressurizing the pumping plate (via the pressure line) and then releasing pressurized air through the solenoid valve in the opposing vacuum line of the pumping plate. A pressure transducer feeds forward a signal to a proportional solenoid valve to allowing an appropriate flow rate of air from the pressurized air source. When the plate has reached the pressure level necessary for sample ejection, the motion controller actuates opening of the solenoid valve for sample ejection.

Correct plate alignment is achieved with magnets and magnetic sensors embedded in the four plates and in the cooling platform. The magnetic sensors must indicate to the motion controller that they are positioned correctly in order to be able to proceed to the following steps of processing run. If they are not, the motion controller dictates motion control steps to reposition the plates and try to proceed. If there is repeated failure, the system stalls to allow manual inspection of the problem.

The integrated processing sequence, identified by the boxed area, indicates the iterated events necessary to complete the chemical processing steps. Namely, it includes the dispense, aspiration, wash and dry commands which are produced by the motion controller. Other process and control commands produced by the main motion controller are the temperature, filtration, ejection and robot motion control commands. Various feedback loops permit precise predetermined control of all systems. It is to be understood that the preferred control system setup is included herein as an example, and could be either slightly modified or vastly different, while nevertheless being able to achieve similar results with the fully automated robot assembly.

In an alternative embodiment, a smaller and more simplified robot is used. This alternative smaller robot does not provide temperature control, and therefore all plate components have significantly reduced mass, and consequently the systems for motion and fluids control are much lighter and more compact. In this case, temperature regulation is achieved by placing the entire automated robotic system within a temperature controlled chamber, which is possible as a result of the compact geometry and reduced mass of the alternative full system permits. Furthermore, electronics and fluids handling are also consequently consolidated and further miniaturized.

The lack of intrinsic temperature regulation in the alternate system, permits the components to be made from non thermally conductive materials. This allows the sample processing plates of the system to be molded into more intricate geometries using a polymeric (or plastic) material. This significantly reduces weight and costs of all components, and enables simplified mass-production of the components. Additionally, certain components can be disposable. For example, the filter plate is packaged with a pre-loaded filter membrane, the entire sub-assembly being disposable after anywhere from a single to several uses. The low cost of the plastic molded plates permits the inexpensive replacement of all parts, permitting for convenient disposability.

An alternative method and structure for coupling and compression of the plates is accomplished by using a simplified mechanism, such as a mechanical clamp for example.

Similar results can also be obtained with several alternative designs. For example, in the first step of sample filtration, multiple samples are loaded onto a surface charged plate having porous wells and separation is completed with a swinging bucket type centrifugation rotor.

In an alternative embodiment, a single multiple well plate is used throughout the procedure, providing that the material of the plate and the other components are chemically compatible with all the processing fluids of the processing protocol. Multiple reservoirs for each of the processing chemicals are used to progressively wash and incubate the samples, where the filtered samples contained in the filter plate are submerged in progressive baths for predetermined time periods. The same container is also used for embedding the processed samples, arriving at similar processing results as the preferred embodiment described in detail above.

The invention claimed is:

1. A parallel processing apparatus for concurrent temperature controlled preparation of a plurality of biological samples adapted to be viewed by an electron microscope, the apparatus comprising:
 a modular core mechanism of plates stackable together in both a first and a second selected configuration, said plates including a filter plate having opposed first and second sides, a pumping plate engaged to the first side of the filter plate, and one of a fluid transfer plate and a sample receiving plate removably engaged to a second side of the filter plate, said first configuration defining said fluid transfer plate being engaged to said second side of the filter plate and said second configuration defining said sample receiving plate being engaged to said second side of the filter plate in place of the fluid transfer plate;
 the filter plate having a plurality of discrete open-ended processing channels extending therethrough between a plurality of first apertures defined in the first of the filter plate and a plurality of second apertures defined in the second side thereof, a sample deposition member transversely extending through each of said processing channels between said opposed first and second apertures for receiving and supporting the biological samples thereon, said sample deposition member allowing fluid flow therethrough in at least a direction towards the first side of the filter plate, said processing channels being individually sealed and isolated from each other such that fluid flow communication therebetween is prevented;
 the pumping plate having at least one nozzle disposed in sealed communication with said first apertures defined in said first side of the filter plate, said nozzle providing a selected one of forced fluid flow and a vacuum to said processing channels, said vacuum providing random sampling deposition of the biological samples onto the sample deposition member and drawing fluids therethrough for evacuation from the processing channels;
 the sample receiving plate including a plurality of closed-bottom wells therein, each well having an opening disposable in sealed communication with each of said second apertures in the second side of the filter plate when the sample receiving plate is engaged thereto;
 the fluid transfer plate defining a plurality of fluid flow channels extending therethrough, said fluid flow channels being individually sealed and isolated from each other such that fluid flow communication therebetween is prevented, each of said fluid flow channels being disposed in fluid flow communication with each corresponding one of said processing channels when the fluid transfer plate is engaged to the second side of the filter plate; and
 a releasable plate interconnection device retaining said plates of the core mechanism fastened together when the plate interconnection device is disposed in a fastening mode and being actuable to switch to a releasing mode wherein at least one of said plates is disengaged from the core mechanism and removable therefrom.

2. The apparatus as defined in claim 1, further comprising an automated robotic assembly including a robotic arm having a plate engaging member being releasably engageable to at least one of said plates of the core mechanism, the robot arm being displaceable to manipulate said at least one of said plates.

3. The apparatus as defined in claim 2, wherein said at least one of said manipulated plates is the said transfer plate, the fluid transfer plate being movable from the core mechanism by the robotic arm when the plate interconnection device is disposed in said releasing mode and replaceable by said sample receiving plate such as to convert the core mechanism from said first configuration to said second configuration.

4. The apparatus as defined in claim 2, wherein plate engaging member of the robotic arm is rotatable at least about 180 degrees about a substantially horizontal axis, wherein the core mechanism is invertable by the robotic arm when the releasable plate interconnection device is disposed in said fastening mode.

5. The apparatus as defined in claim 2, wherein the automated robotic assembly includes a fluid handling means for at least one of inserting and aspirating processing fluid into and out of the processing channels via said fluid flow channels of the fluid transfer plate.

6. The apparatus as defined in claim 5, wherein the fluid handling means includes at least one needle manifold having multiple needles.

7. The apparatus as defined in claim 6, wherein each needle of said needle manifold is independently selectable and controlled by the fluid handling means.

8. The apparatus as defined in claim 1, wherein the plate interconnection device is defined within the core mechanism.

9. The apparatus as defined in claim 1, wherein the plate interconnection device is biased in the fastening mode.

10. The apparatus as defined in claim 9, wherein the plate interconnection device includes an electromagnetic coupling system.

11. The apparatus as defined in claim 10, wherein said electromagnetic coupling system includes at least one permanent magnet disposed in said filter plate and at least one corresponding electromagnetic coupling element disposed in at least each of said fluid transfer plate and said sample receiving plate.

12. The apparatus as defined in claim 11, when said pumping plate includes at least one electromagnetic coupling elements therein corresponding to said permanent magnet of said filter plate.

13. The apparatus as defined in claim 1, further comprising a temperature control device in communication with said core mechanism.

14. The apparatus as defined in claim 13, wherein the temperature control device includes a thermoelectrically temperature controlled incubation member.

15. The apparatus as defined in claim 14, wherein said incubation member includes a cooling platform having a size corresponding substantially to said plates of the core mechanism, said plates being receivable on the cooling platform.

16. The apparatus as defined in claim 1, wherein the sample receiving plate includes a removable multiple-well plate releasably engaged therein, the multiple-well plate comprising said plurality of closed-bottom wells therein.

17. The apparatus as defined in claim 16, wherein the closed-bottomed wells each contain polymerized embedding solution for embedding the biological samples therein after processing within the processing channels by fluids inserted therein.

18. The apparatus as defined in claim 2, wherein the plate engaging member is displaceable by the robotic arm relative to at least four axes to provide at least four-axis motion.

19. The apparatus as defined in claim 18, wherein the plate engaging member is displaceable by the robotic arm relative to five axes to provide five-axis motion.

20. The apparatus as defined in claim 1, wherein the pumping plate comprises a plurality of said nozzles each disposed in sealed communication with one of said processing channels of the filter plate.

21. The apparatus as defined in claim 1, wherein the forced fluid flow provided by said nozzle includes pressurized air, said pressurized air having a pressure sufficient to transfer the cell fraction samples from said filter plate to said wells of said sample receiving plate.

22. The apparatus as defined in claim 1, wherein the sample deposition member includes a filter screen through which fluids can flow.

23. The apparatus as defined in claim 22, wherein the sample deposition member further includes a membrane superimposed on the filter screen, the membrane receiving the biological samples thereon.

24. The apparatus as defined in claim 23, wherein the membrane of the sample deposition member is dissolvable.

* * * * *